(12) United States Patent
Watson et al.

(10) Patent No.: US 6,968,246 B2
(45) Date of Patent: Nov. 22, 2005

(54) METHOD FOR AUTOMATED DESIGN OF ORTHOTIC AND PROSTHETIC DEVICES

(75) Inventors: Keith Watson, Huntsville, AL (US); Marvin Fourroux, Huntsville, AL (US)

(73) Assignee: Fourroux Orthotics & Prosthetics, Inc., Huntsville, AL (US)

(*) Notice: Subject to any disclaimer, the term of this patent is extended or adjusted under 35 U.S.C. 154(b) by 0 days.

(21) Appl. No.: 10/264,835

(22) Filed: Oct. 4, 2002

(65) Prior Publication Data

US 2004/0068337 A1 Apr. 8, 2004

(51) Int. Cl.[7] .................................................. A61F 2/54
(52) U.S. Cl. ...................... 700/98; 700/95; 700/182; 623/23.15
(58) Field of Search .......................... 700/98, 95, 182; 623/23.15, 23.58

(56) References Cited

U.S. PATENT DOCUMENTS

| | | | |
|---|---|---|---|
| 4,821,200 A | | 4/1989 | Oberg |
| 5,025,200 A | * | 6/1991 | Kurakake et al. ............ 318/569 |
| 5,252,822 A | * | 10/1993 | Firth ...................... 250/227.11 |
| 5,258,037 A | | 11/1993 | Caspers |
| 5,432,703 A | * | 7/1995 | Clynch et al. .............. 700/163 |
| 5,522,402 A | | 6/1996 | Cooley |
| 5,529,575 A | | 6/1996 | Klotz |
| 5,534,034 A | | 7/1996 | Caspers |
| 5,539,649 A | | 7/1996 | Walsh et al. |
| 5,552,992 A | * | 9/1996 | Hunter ....................... 700/118 |
| 5,571,208 A | | 11/1996 | Caspers |
| 5,888,216 A | * | 3/1999 | Haberman ................... 623/36 |
| 5,891,545 A | * | 4/1999 | Delude ........................ 428/78 |
| 5,904,722 A | | 5/1999 | Caspers |
| 6,463,351 B1 | * | 10/2002 | Clynch ....................... 700/163 |
| 2002/0016631 A1 | * | 2/2002 | Marchitto et al. ............. 623/7 |

FOREIGN PATENT DOCUMENTS

| | | |
|---|---|---|
| EP | 348 061 B1 | 10/1995 |
| WO | WO 98/18386 | 5/1998 |
| WO | WO 98/30176 | 7/1998 |
| WO | WO 01/85040 A1 | 11/2001 |

OTHER PUBLICATIONS

"A 3D Visualization Tool For Landmark Allocation" -Xue et al, Wright State University, 1999 IEEE.*
"Locating Anatomical Landmarks for Prosthetic Design using Ensemble Neural Networks" -Jimenez et al, The Univeristy of Texas Health Science Center at San Antonio, 1997 IEEE.*

* cited by examiner

*Primary Examiner*—Leo Picard
*Assistant Examiner*—Michael D. Masinick
(74) *Attorney, Agent, or Firm*—David E. Mixon; Bradley Arant Rose & White, LLP (57) ABSTRACT

A method for automated design of orthotic and prosthetic devices has been developed. The method includes scanning a three dimensional model of the patient's limb with a laser scanner. The model is loaded into a computer for use in manufacturing an orthotic or prosthetic device. Before the model is used, it is modified by reducing the overall volume of the model by up to twelve percent of the total volume. Also the model's distal end length is reduced by a calculated percentage of the thickness of a prosthetic liner to be worn with the prosthetic device.

9 Claims, 7 Drawing Sheets

METHOD FOR AUTOMATED DESIGN OF ORTHOTIC AND PROSTHETIC DEVICES

BACKGROUND OF INVENTION

1. Field of the Invention

The invention relates generally to a method for computer aided design. More specifically, the invention relates to automated design for orthotic and prosthetic devices.

2. Background Art

Figure 1A:
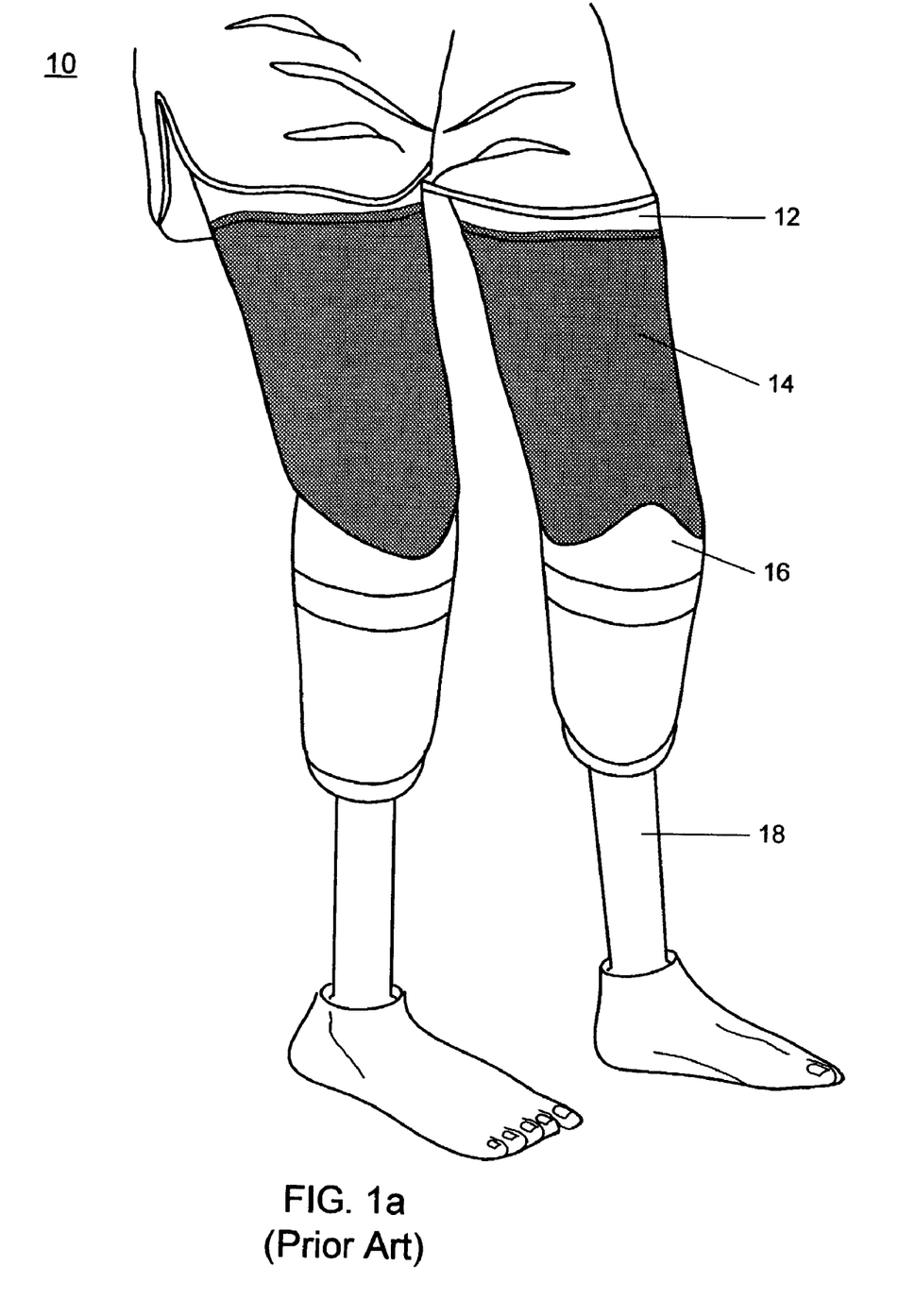
FIG. 1a shows a prior art example of an attached prosthetic limb.
Figure 1B:
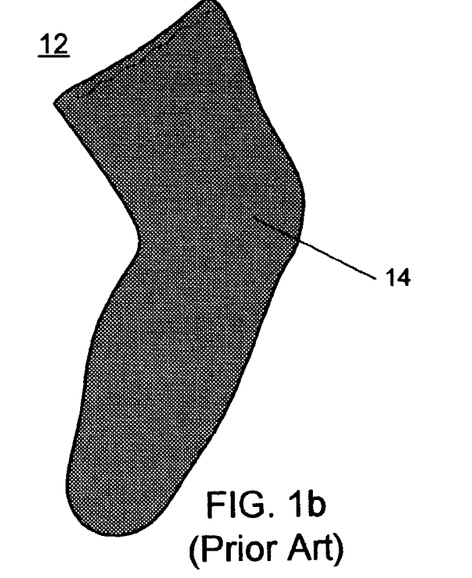
FIG. 1b shows a prior art example of a limb with a liner.
Figure 1C:
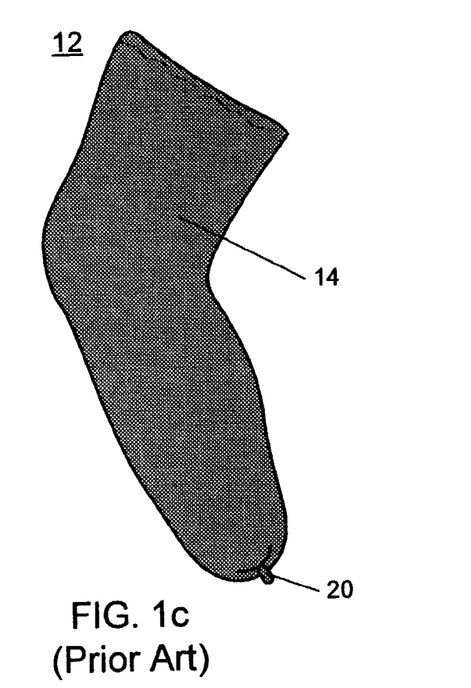
FIG. 1c shows a prior art example of a limb with a liner and a distal end connector.

The design and manufacture of prosthetic and orthotic devices requires custom fitting for a proper and comfortable fit for a patient. FIG. 1 shows a prior art example of an attached prosthetic limb 10. A patient's limb 12 is first fitted with a liner 14. The limb 12 and liner 14 then fit into the socket 16 of the prosthetic limb 18. FIG. 1b shows the patient's limb 12 with the liner 14 before the limb is inserted in the socket. FIG. 1c shows a liner 14 with an optional distal attachment mechanism 20. The mechanism 20 is used to physically attach the liner to the interior of the socket.

The liner is typically made of a malleable gel material, such as urethane or silicone that is sometimes covered on the exterior with a cloth layer called a "wick". The purpose of the liner is to provide cushioning and comfort to the patient. The liner provides a pseudo-hydraulic action that absorbs the energy exerted by gravity and the weight of the patient. The vast majority of the mass of a typical liner is gel while the wick only serves as an exterior cover. A liner is usually tapered in shape with the thickest portion being the distal end. It typically has a decreasing thickness towards the proximal end. The thickness of the liner usually ranges from 2–16 mm. The proximal end thickness typically varies from 2–6 mm, while the distal end thickness varies from 5–16 mm. However, the thickness may vary outside these ranges based on the needs of the individual patient.

Figure 2:
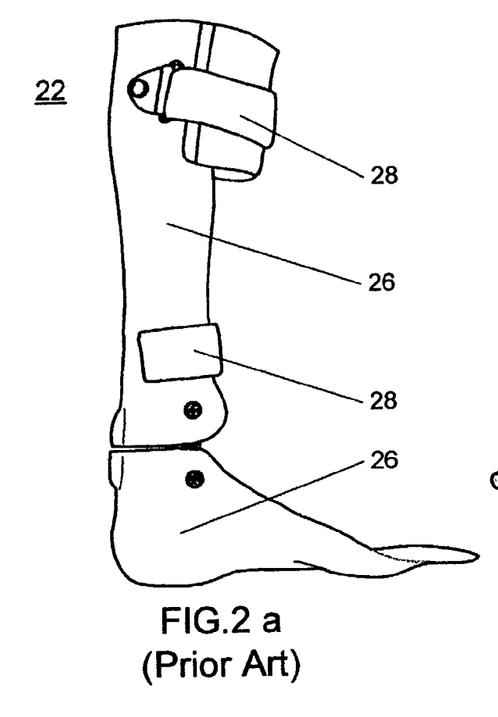
FIGS. 2a and 2b show prior art examples of a fitted orthosis.

FIGS. 2a and 2b show a prior art example of a custom molded orthosis 22. The patient's limb fits into a frame 26 that is customized for the individual patient. The limb is held in place by multiple straps 28. The limb may also be covered with a liner or similar device to ensure a comfortable fit and provide protection for the limb. An orthosis of the type shown is typically used to support and stabilize the compromised limb.

Prior art methods of customizing prosthetic and orthotic devices for individual patients involved taking an anatomical impression of the patient's limb. The impression is made by taking a casting of the patients' limb by wrapping the limb with plaster wrappings. After drying, the casting is removed from the limb and a model of the limb is made by using the casting as a mold. The model of the limb is the used to fashion a customized prosthetic or orthotic device for the patient.

Even with a skilled practitioner, the casting of the limb is messy, time-consuming, and it is prone to errors. Typically, the casting practitioner must manipulate the limb's soft tissue and bony prominences to achieve a proper anatomical alignment. This technique often requires multiple re-castings due to inconsistencies in the alignment.

SUMMARY OF INVENTION

In some aspects, the invention relates to a method for creating a representation of a limb suitable for constructing a prosthetic device, comprising: scanning a three dimensional representation of the limb into a computer system; reducing the volume of the three dimensional representation of the limb by up to twelve percent of the total volume of the limb; and reducing the distal length of the three dimensional representation of the limb by a calculated percentage of the distal thickness of a prosthetic liner to be worn with the prosthetic device.

In other aspects, the invention relates to a method for creating a representation of a limb suitable for constructing a prosthetic device, comprising: step for creating a representation of the limb with a computer system; step for reducing the volume of the representation of the limb; and step for reducing the distal length of the representation of the limb.

In other aspects, the invention relates to a method for creating a representation of a limb suitable for constructing an orthotic device, comprising: scanning a three dimensional representation of the limb into a computer system; and identifying boney prominences of the limb that are suitable for an overlay.

In other aspects, the invention relates to a method for creating a representation of a limb suitable for constructing an orthotic device, comprising: step for creating a representation of the limb with a computer system; and step for identifying areas of the limb that are suitable for an overlay.

In other aspects, the invention relates to a method for creating a representation of a limb suitable for constructing a prosthetic liner, comprising: scanning a three dimensional representation of the limb into a computer system; and transmitting the three dimensional representation of the limb to a manufacturing facility for the prosthetic liner.

In other aspects, the invention relates to a method for creating a representation of a limb suitable for constructing a prosthetic liner, comprising: step for creating a representation of the limb with a computer system; and step for using the representation of the limb to manufacture a customized prosthetic liner.

Other aspects and advantages of the invention will be apparent from the following description and the appended claims.

BRIEF DESCRIPTION OF DRAWINGS

It should be noted that identical features in different drawings are shown with the same reference numeral.

DETAILED DESCRIPTION

Figure 3:
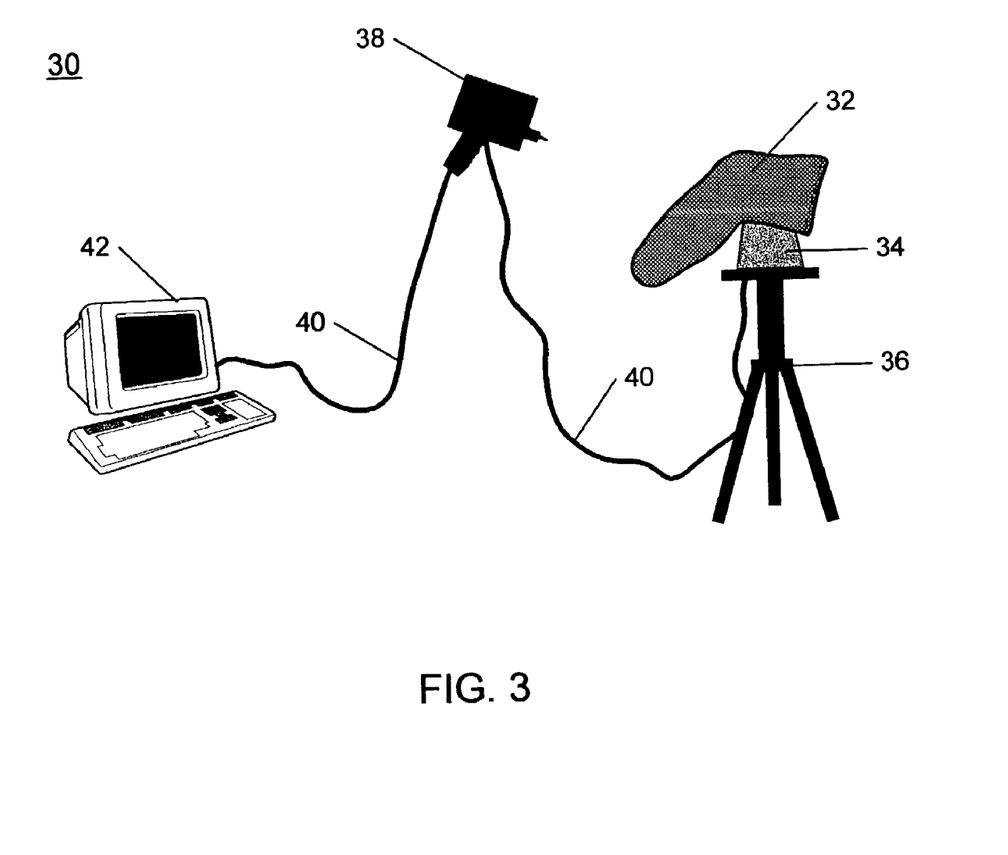
FIG. 3 shows a schematic of one embodiment of the present invention with the equipment for automated design of a prosthetic device.

A method for automated design for orthotic and prosthetic devices has been developed that has a high degree of accuracy in modeling the patients' limb. FIG. 3 shows a schematic of one embodiment of the present invention with the equipment for an automated design system 30 for a prosthetic device. In this embodiment, the patient's limb 32 rests on a positioning transmitter 34 that is supported by a stand 36. A laser scanner 38 scans the surface of limb and records its dimensions. The patient wears a sock over the limb 32 that reflects the light from laser. In some embodiments, the patient may wear multiple socks or a single sock with multiple layers. The sock is typically made of white cotton that is capable of reflecting laser light. The positioning transmitter 34 generates a relative position of the limb 32 to the scanner 38 through an attached cable 40. The scanner 38 then collects the dimensions of the limb 32 and transmits them via cable 40 to a computer 42.

Figure 4A:
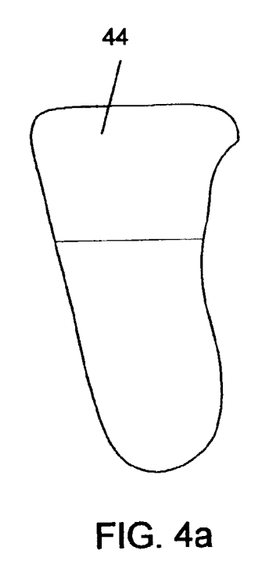
FIGS. 4a, 4b, and 4c show computer generated views of the patient's limb in accordance with one embodiment of the present invention.
Figure 4B:
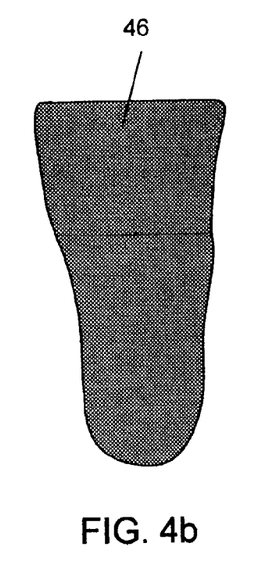
Figure 4C:
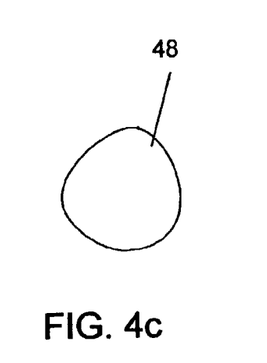

At the computer, the dimensions of the limb are analyzed with custom software that generates a three dimensional representation of the patient's limb. FIGS. 4a, 4b, and 4c show examples of three separate views of the limb generated by the computer. FIG. 4a shows an outline of a frontal view of the limb 44. FIG. 4b shows a three dimensional frontal view of the limb 46. Finally, FIG. 4c shows an overhead cross-sectional view of the limb 48.

Before the computer representations of the limb 44, 46, and 48 can be used to manufacture a prosthetic device, modifications need to be made to ensure a proper fit. These modifications necessary to compensate for the presence of the liner as well as any redundant tissue on the residual end of the patient's limb. As a patient wears a liner throughout the day, the size of the limb changes due to the activity of the patient. This variation in limb size can result in the fit of the prosthetic device becoming loose and uncomfortable for the patient. In order to compensate for the change in size, the computer representations of the limb should be adjusted by the computer.

Figure 5A:
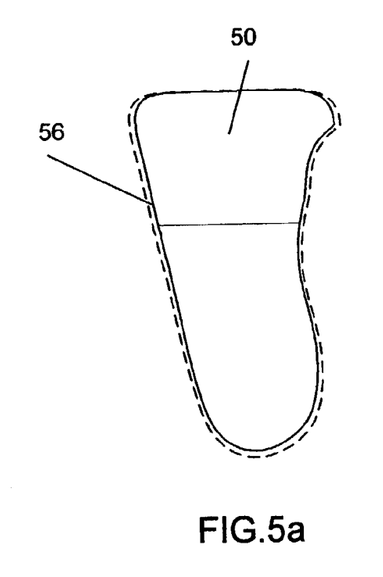
FIGS. 5a, 5b, and 5c show computer generated views of the patient's limb with the volumetric adjustments in accordance with one embodiment of the present invention.
Figure 5B:
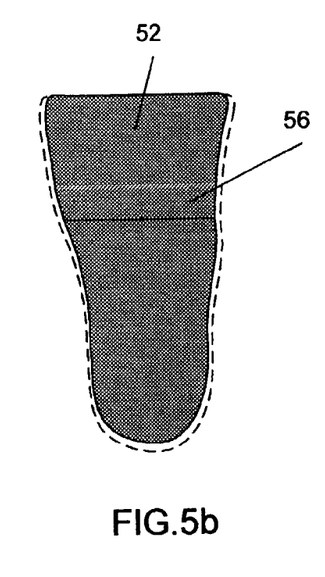
Figure 5C:
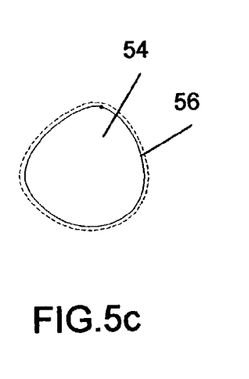

First, the overall volume of the limb should be reduced in volume by up to 12 percent. In some alternative embodiments, the volume is reduced by about 3 to 5 percent. FIGS. 5a, 5b, and 5c show examples of three separate views that are generated by the computer of the limb after the volume reduction. Each view corresponds with the similar view shown in FIGS. 4a, 4b, and 4c before the volume reduction. Specifically, FIG. 5a shows an outline of the frontal view 50 of the limb after a volume reduction 56. FIG. 5b shows a three dimensional frontal view 52 of the limb after a volume reduction 56. FIG. 5c shows an overhead cross-sectional view 54 of the limb after a volume reduction 56. While the reduction of volume is normally as much as 12 percent of the total limb volume, it should be noted that amount of the reduction may vary somewhat outside this range in alternative embodiments.

Figure 6A:
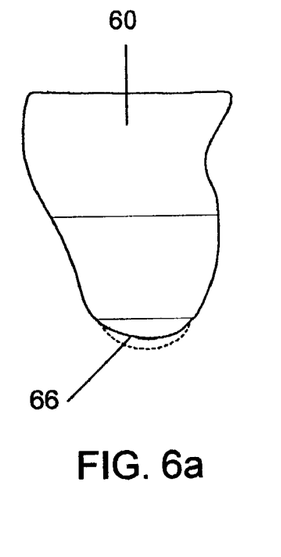
FIGS. 6a, 6b, and 6c show computer generated views of the patient's limb with the distal length adjustments in accordance with one embodiment of the present invention.
Figure 6B:
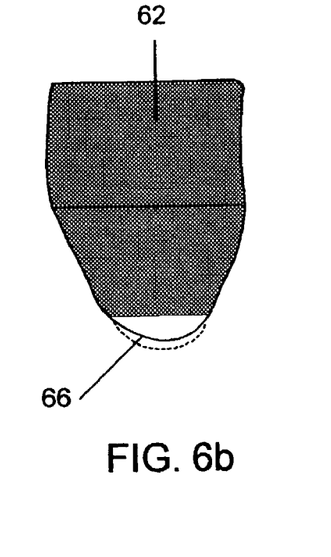
Figure 6C:
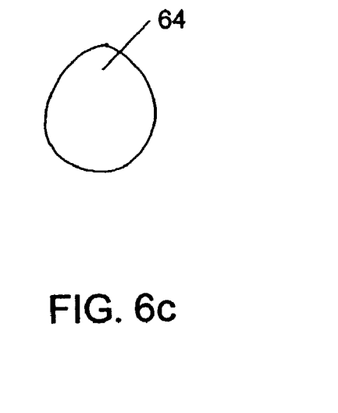

Next, the distal length of the model should be reduced. FIGS. 6a, 6b, and 6c show examples of three separate views that are generated by the computer of the limb after the distal length reduction. Each view corresponds with the similar view shown in FIGS. 4a, 4b, and 4c before the distal length reduction. Specifically, FIG. 6a shows an outline of the frontal view 60 of the limb after a distal length reduction 66. FIG. 6b shows a three dimensional frontal view 62 of the limb after a distal length reduction 66. FIG. 6c shows an overhead cross-sectional view 64 of the limb after a distal length reduction 66. The distal length reduction is a calculated percentage of the thickness of the liner. Many different types of liners are commercially available. Consequently, the typical distal end thickness of a liner may range from 4 mm–16 mm. The percentage of reductions are calculated based on the characteristics of the individual liners. Such factors in the calculations include: thickness; type of material; softness levels; compressibility; rebound rate; elasticity; reaction to temperature, etc. These factors are usually provided by the liner manufacturers. As a result, the factors used for different liners may vary widely in their use and relative weight in calculations.

A typical calculation would result in a distal length reduction of about 2 mm–8 mm of the computer representation of the limb. However, other liners could have a thickness outside the normal range of thickness and the distal reduction would vary accordingly. While the reduction of the distal length is normally about 2 mm–8 mm or some other calculated percentage of the thickness of the liner, it should be noted that the amount of the reduction may be somewhat greater or less in alternative embodiments.

Figure 7A:
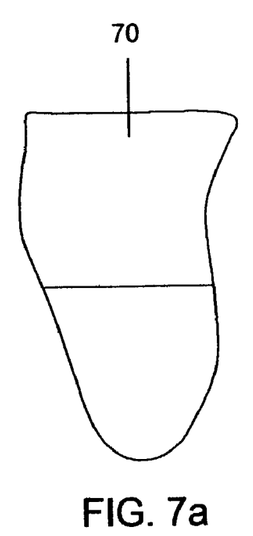
FIGS. 7a, 7b, and 7c show computer generated views of the patient's limb with the bony prominences identified in accordance with one embodiment of the present invention.
Figures 7B, 7C:
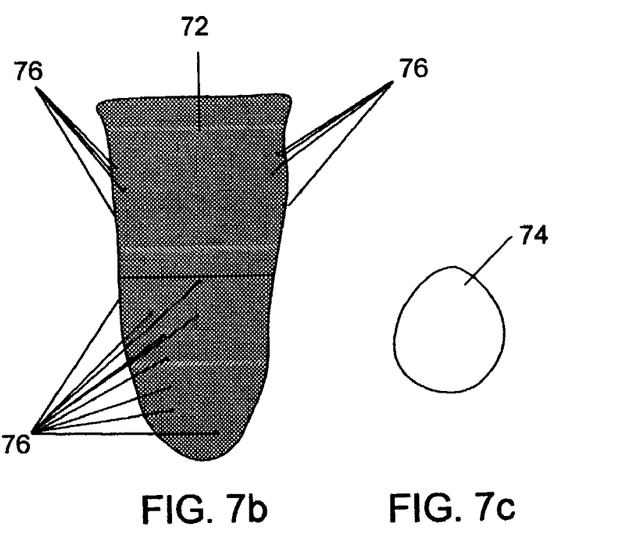

Finally, boney prominences of the limb are mapped. These may include areas, such as the patella (or "knee-cap"), where the underlying bone is close to the skin of the patient. FIGS. 7a, 7b, and 7c show examples of three separate views that are generated by the computer of the limb after the boney landmark mapping. Each view corresponds with the similar view shown in FIGS. 4a, 4b, and 4c. Specifically, FIG. 7b shows a three dimensional frontal view 72 of the limb after the boney prominences 76 are landmarked. The prominences 76 are not shown in FIGS. 7a and 7c.

Figure 8A:
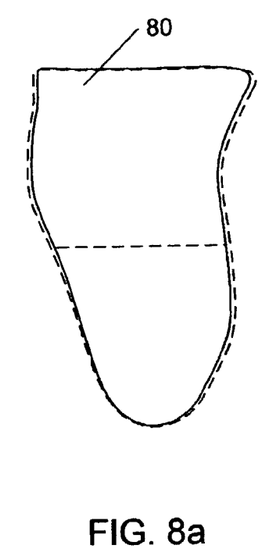
FIGS. 8a, 8b, and 8c show computer generated views of the patient's limb with the areas of overlay adjustments identified in accordance with one embodiment of the present invention.
Figures 8B, 8C:
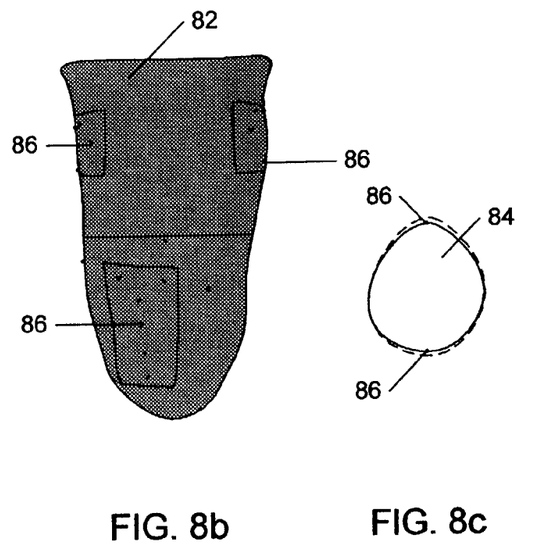

After the landmarking, the computer software automatically identifies the areas of the limb that need an overlay. Typically, areas that need an overlay are areas with landmarks clustered relatively close together. FIGS. 8a, 8b, and 8c show examples of three separate views of the limb after the overlay regions are identified by the computer. Each view corresponds with the similar view shown in FIGS. 4a, 4b, and 4c. Specifically, FIG. 8a shows an outline of the frontal view 80 of the limb after the overlay regions 86 are marked. FIG. 8b shows a three dimensional frontal view 82 of the limb after the overlay regions 86 are marked. FIG. 8c shows an overhead cross-sectional view 84 of the limb after the overlay regions are marked 86.

Once the computer modifications are made to the representations of the limb, the data is transmitted to a manufacturing facility. The customized prosthetic socket is then constructed based on this information. The prosthetic limb is constructed with minimal inconvenience to the patient since the measurements of the limb are taken quickly and accurately. The modifications to the measurements of the limb result in a comfortable, better fitting prosthetic limb for the patient. The need for re-measurement or adjustment of the socket is minimal with the present invention.

It should be noted that in alternative embodiments, the modifications to the representations of the limb can be done in any order. It also should be noted that in alternative embodiments, the identification of boney prominences may be skipped. While the embodiments shown have dealt only with a leg amputation below the knee, it should be noted that the present invention could be applied in other situations such as a prosthetic arm or an above the knee amputation.

Figure 9:
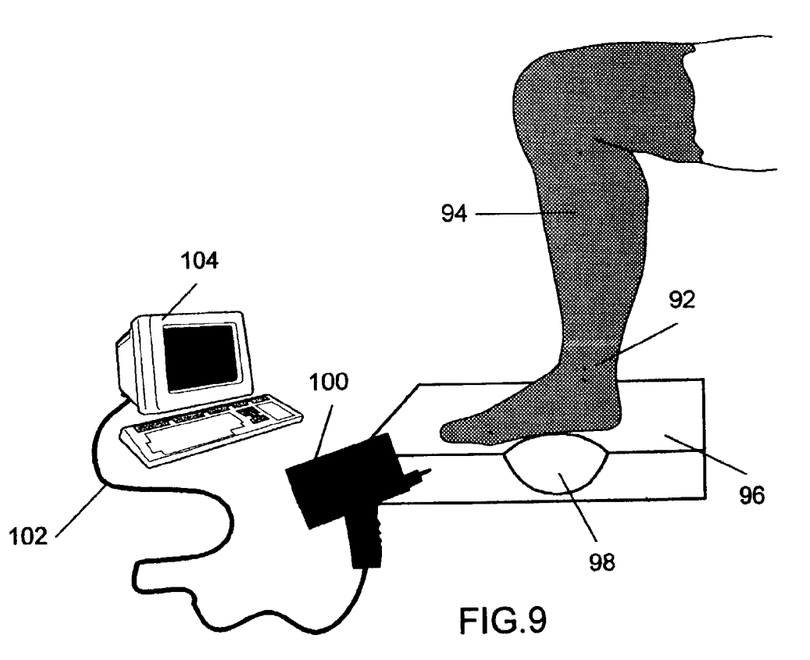
FIG. 9 shows a schematic of one embodiment of the present invention with the equipment for automated design of an orthotic device.

FIG. 9 shows a schematic of one embodiment of the present invention with the equipment for an automated design system 90 for an orthotic device. In this embodiment, the patient places his foot 92 on a foot block 96. The patient wears at least one or more socks 94 over his foot. The sock 94 is typically made of white cotton that is capable of reflecting laser light. The patient places his foot over a concave portion 98 of the foot block 96. The concave portion 98 allows scanning of the arch of the foot 92. A laser scanner 100 is used to scan the dimensions of the patient's foot 92 into a computer 104 via a cable connection 102 in a similar manner as described in FIG. 3.

Figure 10A:
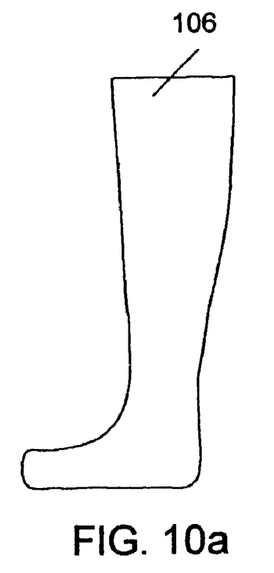
FIGS. 10a, 10b, and 10c show computer generated views of the patient's limb with the bony prominences identified in accordance with one embodiment of the present invention.
Figure 10B:
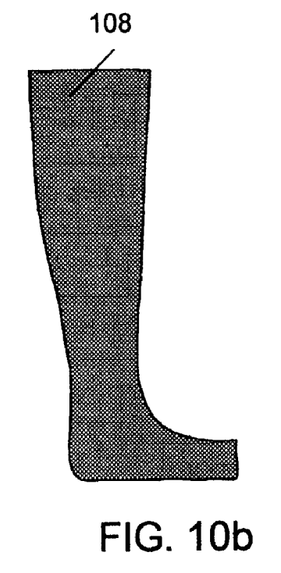
Figure 10C:
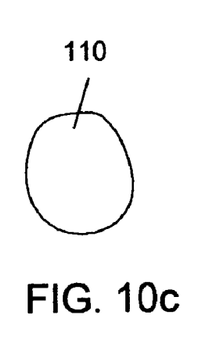

At the computer, the dimensions of the foot are analyzed with custom software that generates a three dimensional representation of the patient's foot. FIGS. 10a, 10b, and 10c show examples of three separate views of the foot generated by the computer. FIG. 10a shows an outline of a side view of the foot 106. FIG. 4b shows a three dimensional side view of the foot 108. Finally, FIG. 4c shows an overhead cross-sectional view of the foot 110.

Before the computer representations of the foot 106, 108, and 110 can be used to manufacture an orthosis, modifications need to be made to ensure a proper fit. Specifically, boney prominences 111 of the foot are mapped for boney landmarks as shown in FIG. 10b. These may include areas such as the ankle, where the underlying bone is close to the skin of the patient. These areas are mapped in order to provide additional overlays of material. This provides greater comfort to the patient by providing extra thickness of material over the boney landmarks. The mapping is done in a similar manner as previously described for FIGS. 7a–7c and FIGS. 8a–8c.

Figure 11A:
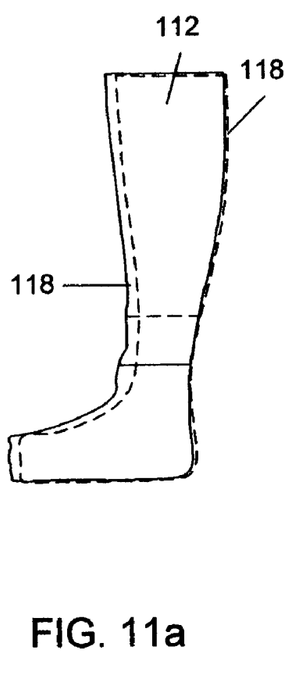
FIGS. 11a, 11b, and 11c show computer generated views of the patient's limb with the areas of overlay adjustments identified in accordance with one embodiment of the present invention.
Figure 11B:
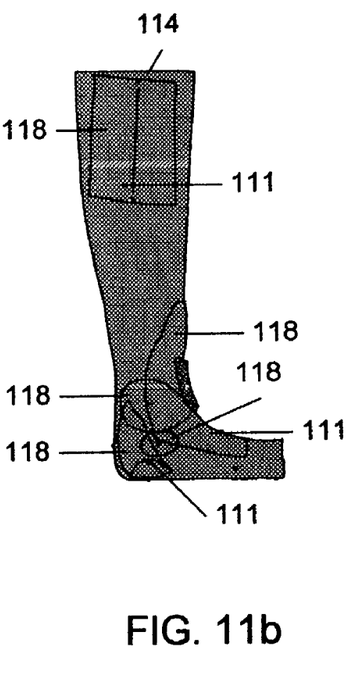
Figure 11C:
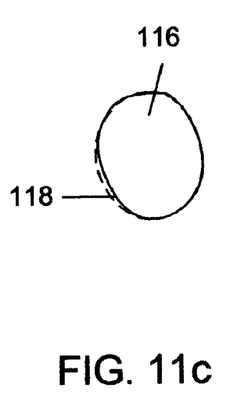

After the landmarking, the computer software automatically identifies the areas of the foot that need an overlay. FIGS. 11a, 11b, and 11c show examples of three separate views of the foot after the overlay regions 118 are identified by the computer. Each view corresponds with the similar view shown in FIGS. 10a, 10b, and 10c. Specifically, FIG. 11a shows an outline of the side view 112 of the foot after the overlay regions 118 are marked. FIG. 11b shows a three dimensional side view 114 of the foot after the overlay regions 118 are marked. FIG. 11c shows an overhead cross-sectional view 116 of the foot after the overlay regions are marked 118.

Once the computer modifications are made to the representations of the foot, the data is transmitted to a manufacturing facility. The customized orthosis is then constructed based on this information. The orthosis is constructed with minimal inconvenience to the patient since the measurements of the foot are taken quickly and accurately. The modifications to the measurements of the foot result in a comfortable, better fitting orthosis for the patient. The need for re-measurement or adjustment of the orthotic frame is minimal with the present invention.

In alternative embodiments, the method of scanning the limb described previously can be used to provide a model for a custom liner for the patient's limb. The limb is scanned in the same manner as previously described and shown in FIG. 3. After scanning, the computer representations of the limb are transmitted to a liner manufacturing facility. Typically, modifications to the computer representations are not necessary when creating a customized liner. However, in alternative embodiments, modifications to the dimensions of the liner could be made in order to ensure an optimized fit. A customized liner is then manufactured to correspond to the specific dimensions of the patient's limb. This results in a better fitting, more comfortable liner.

While the embodiments shown have dealt only with an orthosis for a foot, it should be noted that the present invention could be applied in other situations such as an orthotic devices for the knees, arms, the face, or the head. It should be clear that any part of the body can be scanned and modified in the methods described here. Alternative embodiments can be used to construct burn garments and other therapeutic or protective devices.

While the invention has been described with respect to a limited number of embodiments, those skilled in the art, having benefit of this disclosure, will appreciate that other embodiments can be devised which do not depart from the scope of the invention as disclosed here. Accordingly, the scope of the invention should be limited only by the attached claims.

What is claimed is:

1. A method for creating a representation of a limb suitable for constructing a prosthetic device, comprising:
    scanning a three dimensional representation of the limb into a computer system;
    reducing the volume of the three dimensional representation of the limb by up to twelve percent of the total volume of the limb; and
    reducing the distal length of the three dimensional representation of the limb by a calculated percentage of the distal thickness of a prosthetic liner to be worn with the prosthetic device.

2. The method of claim 1, further comprising:
    identifying boney prominences of the limb that are suitable for an overlay.

3. The method of claim 1, where the limb is an amputated leg.

4. The method of claim 3, where the leg is amputated below the knee.

5. The method of claim 1, where limb is scanned by a laser scanner.

6. The method of claim 1, where volume of the representation is reduced between three and five percent of the total volume of the limb.

7. The method of claim 1, where the distal length of the representation is reduced by between 2 millimeters and 8 millimeters.

8. A method for creating a representation of a limb suitable for constructing a prosthetic device, comprising:
    step for creating a representation of the limb with a computer system;
    step for reducing the volume of the representation of the limb; and
    step for reducing the distal length of the representation of the limb by a calculated percentage of the distal thickness of a prosthetic liner to be worn with the prosthetic device.

9. The method of claim 8, further comprising:
    step for identifying areas of the limb suitable for an overlay.

* * * * *